US006109484A

United States Patent [19]

Sueoka et al.

[11] Patent Number: 6,109,484

[45] Date of Patent: Aug. 29, 2000

[54] DROPPING CONTAINER

[75] Inventors: Eizo Sueoka; Hiroshi Nishimura; Masami Arata, all of Moriyama, Japan

[73] Assignee: Sun Medical Co Ltd, Shiga-ken, Japan

[21] Appl. No.: 09/038,979

[22] Filed: Mar. 12, 1998

[30] Foreign Application Priority Data

Mar. 14, 1997 [JP] Japan .................................... 9-061057

[51] Int. Cl.[7] ............................... B67D 5/42; A61C 5/04; A61M 35/00

[52] U.S. Cl. .......................... 222/390; 222/386; 222/518; 433/90; 604/311

[58] Field of Search ..................................... 222/386, 390, 222/518; 433/80, 81, 89, 90; 239/86; 604/295, 298, 311

[56] References Cited

U.S. PATENT DOCUMENTS

| | | | |
|---|---|---|---|
| 3,087,656 | 4/1963 | Dougherty | 222/518 |
| 3,658,216 | 4/1972 | Schwartzman | 222/518 X |
| 3,961,731 | 6/1976 | Mochida | 222/390 |
| 4,813,870 | 3/1989 | Pitzen et al. | 222/390 X |
| 4,973,248 | 11/1990 | Sigler | 433/90 |
| 5,547,131 | 8/1996 | Brace | 222/390 X |

FOREIGN PATENT DOCUMENTS

| | | |
|---|---|---|
| 0526824 | 2/1993 | European Pat. Off. . |
| 379945 | 11/1907 | France . |
| 561574 | 10/1923 | France . |
| 29 60 997 9 U | 11/1997 | Germany . |
| 50-139498 | of 1975 | Japan . |
| 5-65900 | 8/1993 | Japan . |
| WO9210425 | 6/1992 | WIPO . |

*Primary Examiner*—Henry J. Recla
*Assistant Examiner*—Kathleen J. Prunner

[57] ABSTRACT

A dropping container includes a cylindrical body, a dropping portion having a pressure valve for closing an opening in the dropping container body such that it can be opened by pressure and a thin tube which is open to the outside. The pressure valve includes a sealing plug portion formed of an elastic body or a rigid body and a pressing member, formed of an elastic body, for pressing the sealing plug portion against the opening to close the opening, a movable plug supplies the content of the cylindrical body to the dropping portion.

7 Claims, 3 Drawing Sheets

DROPPING CONTAINER

BACKGROUND OF THE INVENTION

The present invention relates to a dropping container and, more specifically, to a dropping container for containing an unstable substance which reacts, decomposes or fumes when it contacts air and for dropping the substance upon use.

Japanese Patent Publication No. 42-12318 (12,318/1967) discloses that an acrylic resin adhesive comprising alkylboron as a curing agent shows strong adhesion to a bone and a tooth and is useful for dental and surgical applications.

However, the alkylboron used as a curing agent is an unstable substance which readily reacts with oxygen in the air and loses its activity thereby. A curing agent which overcomes this defect is disclosed by Japanese Patent Publication No. 51-37092 (37,092/1976).

That is, Japanese Patent Publication No. 51-37092 discloses an adhesive filler for dental and surgical applications which comprises a product obtained by reacting trialkylboron with 0.3 to 0.9 mol of oxygen as a curing agent.

The product as a curing agent is used to suppress the adhesion of trialkylboron to the least possible degree so as to remove the ignitability of the trialkylboron. However, this product is also an unstable substance, though not so unstable as trialkylboron.

Hitherto, such an unstable substance has been preserved in a closed ampul, and the ampul has been broken on use and sealed up again after use. However, it takes much time and labor to break and seal up the ampul. In addition, since the unstable substance in the ampul contacts air even for a short period of time from the breakdown to the sealing of the ampul, it has often reacted with air to lose its activity.

To overcome the above defect, Japanese Laid-open Utility Model Application No. 50-139498 (139498/1975) discloses a dropping container in which a closing portion having a thin tube for dropping is provided at one end of a cylindrical body made from a metal or glass and a movable plug made from fluororubber or fluororesin is provided near the other end, and the movable plug is pushed by rotating a screw attached to the cylindrical body or a container for mounting the cylindrical body to take out a predetermined amount of a curing agent filled in the cylindrical body.

This container enables a required amount of alkylboron to be taken out by dropping. However, since a curing agent present in the thin tube for dropping contacts the outside air through an opening at the tip of the thin tube, it is almost impossible to prevent the curing agent from deteriorating gradually even with the tip capped when it is preserved for a long time.

Further, Japanese Laid-open Utility Model Application No. 5-65900 (65,900/1993) discloses a dropping container having such a structure that entry of air from the outside can be inhibited almost perfectly to prevent the deterioration of a curing agent when it is preserved for a long time.

However, since this dropping container has such a structure that it is sealed up by an elastic body itself to preserve a chemical, the elastic body may deteriorate due to the chemical through its long-time use.

SUMMARY OF THE INVENTION

It is therefore an object of the present invention to provide a dropping container having a novel structure.

It is another object of the present invention to provide a dropping container having such a structure that it is sealed up by an elastic body or a rigid body to preserve a chemical.

It is still another object of the present invention to provide a dropping container which can be used continuously smoothly for a long time.

It is still another object of the present invention to provide a dropping container having such a structure that entry of air from the outside can be inhibited almost perfectly.

It is still another object of the present invention to provide a dropping container which has little dead space and, thereby reducing a wasted chemical such as a curing agent after use to an amount as small as possible.

It is still another object of the present invention to provide a dropping container which enables a required amount of a curing agent, for example, to be taken out by dropping while achieving the above advantages.

It is still another object of the present invention to provide a dropping container which does not deteriorate a chemical such as a curing agent through long-time preservation and consequently, can supply continuously its content having activity maintained, such as a curing agent, stably over a long period of time.

Further objects and advantages of the present invention should be apparent from the following description.

According to the present invention, firstly, the above objects and advantages can be attained by a dropping container which comprises a pressure valve for closing an opening in a dropping container body so that it can be opened by pressure, the pressure valve comprising a sealing plug portion formed of an elastic body or a rigid body and a pressing member, formed of an elastic body, for pressing the sealing plug portion against the opening to close the opening.

The dropping container of the present invention comprises a pressure valve and a dropping portion having a thin tube which is open to the outside, as described above.

The pressure valve has a sealing plug portion formed of an elastic body or a rigid body. The pressure valve closes an opening in the dropping container body with the sealing plug portion such that it can be opened by pressure. When the opening is opened by pressure, a substance to be dropped filled in the dropping container body, such as alkylboron as described above, is dropped from the dropping container through the opened opening and then the thin tube which is open to the outside.

The sealing plug portion of the pressure valve is formed of an elastic body or a rigid body as described above. Illustrative examples of the elastic body include natural rubber and synthetic rubber and illustrative examples of the rigid body include fluororesin, stainless steel, polyolefin resins and metal oxides.

The opening in the dropping container body and the sealing plug portion of the pressure valve are preferably in surface contact or circular line contact with each other to close the opening.

The dropping container of the present invention preferably further is provided with a spacer in space for accommodating the above sealing plug portion and pressing member, that is, pressure valve, to reduce dead space in the space. The spacer may be integrated with the sealing plug portion of the pressure valve. The sealing plug portion of the pressure valve may also be integrated with the pressing member.

The above pressing member is formed of an elastic body. The pressing member may be formed of, for example, a coil spring, a flat spring or an elastic body such as natural or synthetic rubber. The pressing member works to press the sealing plug portion against the opening to close the opening in the dropping container body.

The content of the cylindrical body is pressed by the movable plug, enters the dropping portion by opening the pressure valve and is dropped through the thin tube which is open to the outside.

The inner diameter of the thin tube is suitably determined by the weight (or volume) of one drop required, the viscosity of the content, or the like, while it is generally about 0.1 to 3 mm.

The length of the thin tube is also suitably selected as required, while it is generally about 1 to 20 mm.

The thin tube is made from, for example, iron plated with nickel.

According to the present invention, a preferred embodiment of the present invention is a dropping container comprising:

(a) a cylindrical body (1);

(b) the first closing portion (2) for closing one end of the cylindrical body (1), the first closing portion (2) having a projecting portion (4) which projects from the cylindrical body (1) in an axial direction of the cylindrical body (1), the first closing portion (2) and the projecting portion (4) having the first thin tube (3) extending therethrough, the first thin tube (3) having an opening (5) at one end thereof at the tip in a longitudinal direction of the projecting portion (4) and an opening (5') at the other end in the first closing portion (2) within the cylindrical body (1); the first thin tube (3) is unobstructed;

(c) a pressure valve comprising a sealing plug portion (6), formed of an elastic body or a rigid body, for closing the opening (5) of the projecting portion (4) such that it can be opened by pressure and a pressing member (7), formed of an elastic body, for pressing the sealing plug portion (6) against the opening (5);

(d) a dropping portion (9) having the second thin tube (8) therein, the dropping portion (9) that encases the projecting portion (4) and the pressure valve and is fitted to the projecting portion (4), the opening (10) of the second thin tube (8) at one end being open to the interior of the dropping portion (9) and the opening (10') thereof at the other end being open to the outside;

(e) a plug (11) movable in the axial direction, that is situated within the cylindrical body (1); and (f) The second closing portion (13) which is fixed at the other end of the cylindrical body (1) and has pressing means (12) for pressing the movable plug (11) toward the first closing portion (2).

DETAILED DESCRIPTION OF THE INVENTION

The dropping container of the present invention will be described hereinafter with reference to the accompanying drawings.

Figure 1:
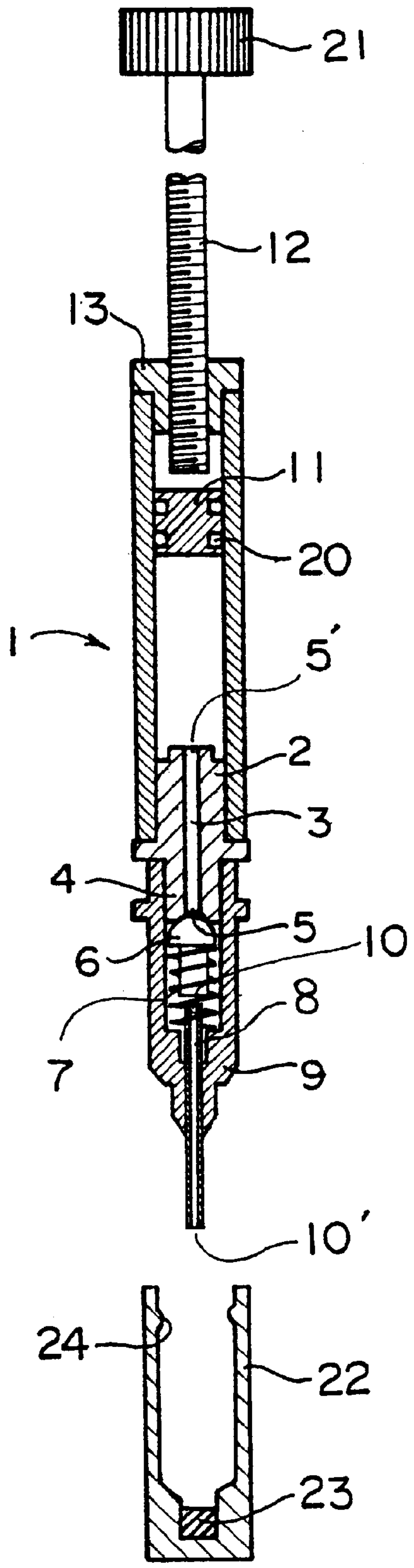
FIG. 1 is a schematic diagram for explaining the structure of the dropping container of the present invention.

FIG. 1 is a schematic sectional view for explaining the structure of the dropping container of the present invention.

Reference numeral (1) denotes a cylindrical body, (2) the first closing portion, (3) the first thin tube, (4) a projecting portion, (5) and (5') openings, (6) a sealing plug portion of a pressure valve, (7) a pressing member of the pressure valve, (8) the second thin tube, (9) a dropping portion, (10) and (10') openings, (11) a movable plug, (12) pressing means and (13) the second closing portion.

The cylindrical body (1) is made from, for example, glass, a suitable synthetic resin or metal. These materials are required to have the following properties. That is, (i) it must not change the quality of the content, (ii) it must be hardly damaged at the time of production, and (iii) it must be transparent so that content can be seen. Therefore, the cylindrical body (1) is preferably made from a transparent material, particularly preferably transparent glass. The first closing portion (2) closes one end of the cylindrical body (1). The cylindrical body (1) and the first closing portion (2) can be fixed by, for example, a thermosetting resin-based adhesive. The first closing portion (2) is preferably made from a metal such as brass plated with nickel. The first closing portion (2) has the first thin tube (3) extending therethrough. The first thin tube (3) may be integrated with the first closing portion (2) or may be fixed to the first closing portion (2) as a part separate from the first closing portion (2).

The first closing portion (2) has the projecting portion (4) which projects from the cylindrical body (1) toward the axial direction of the cylindrical body (1). The first closing portion (2) and the projecting portion (4) have the first thin tube (3) extending therethrough, and the first thin tube (3) has the opening (5) at one end thereof at the tip in a longitudinal direction of the projecting portion (4) and the opening (5') at the other end in the first closing portion (2) within the cylindrical body (1). In other words, the projecting portion (4) has the opening (5) of the first thin tube (3) at the tip in a longitudinal direction. The openings (5') and (5) serve as an inlet and outlet for taking out a filling material filled in the cylindrical body (1) through the first thin tube (3), respectively. The opening (5) is preferably a tapered opening.

Figure 2:
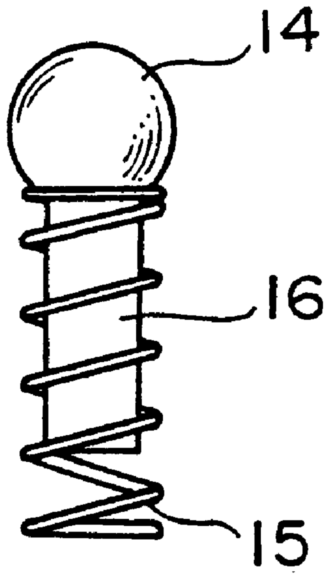
FIG. 2 is a schematic diagram of an embodiment of a pressure valve used in the present invention.
Figure 4:
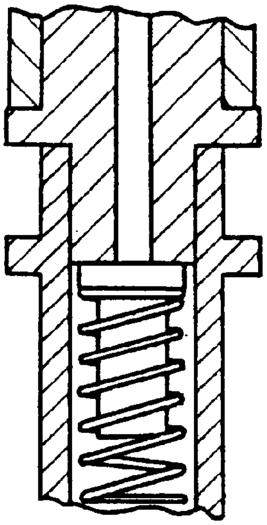
FIG. 4 is a schematic diagram of an embodiment showing the relationship between an opening and a rigid body used in the present invention.
Figure 5:
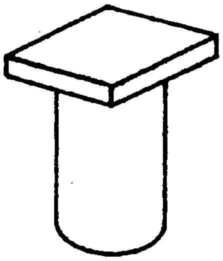
FIG. 5 is a schematic diagram of another embodiment of a pressure valve used in the present invention.
Figure 6:
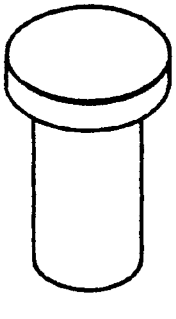
FIG. 6 is a schematic diagram of another embodiment of a pressure valve used in the present invention.

The projecting portion (4) of the first thin tube (3) is mated with the dropping portion (9) having the second thin tube (8). Inside the dropping portion (9), there is space between the projecting portion (4) and the second thin tube. The pressure valve comprising the sealing plug portion (6) formed of an elastic body or a rigid body and the pressing member (7) formed of an elastic body lies in this space. The sealing plug portion (6) of the pressure valve is pressed in a fully liquid-filled state against the opening of the dropping container body, that is, the opening (5) of the first thin tube (3), to close the opening (5). A spacer may be provided in the space to reduce dead space. For example, the pressure valve shown in FIG. 2 comprises a sealing plug portion (14), an elastic body (15) for pressing the sealing plug portion (14) against the opening (5), and a spacer (16). That is, it is the elastic body (15) which presses the sealing plug portion (14) against the opening (5) in a fully liquid-filled state. When the opening (5) is tapered, the sealing plug portion (14) has such a shape that it can contact the opening (5) in a fully liquid-filled state such as a spherical shape, semi-spherical shape, spherical or semi-spherical shape having a dented top portion. The tapered portion of the opening (5) and the sealing plug portion are pressed against each other in a fully liquid-filled state by circular line contact. When the opening (5) is not tapered as shown in FIG. 4, a sealing plug portion having a circular or square top surface as shown in FIG. 5 or FIG. 6 may be used. These sealing plug portions are pressed against the opening in a fully liquid-filled state by surface contact. Further, the opening (5) may be structured such that liquid-tightness can be maintained on a concave or convex surface. Out of these, circular line contact is preferred.

The material of the sealing plug portion (14) is selected from metals such as 18-8 stainless steel, metal oxides such as ruby, alumina oxide, zirconium oxide, silicon nitride, silicon oxide and glass, and synthetic resins such as polyethylene, polypropylene, nylon and fluororesin. Out of these, a material which does not react with the content and does not swell is suitably selected and used.

The elastic body has a function to press the sealing plug portion against the opening (5) in the space and can be, for example, a coil spring, a flat spring or rubber molding. Out of these, a coil spring and flat spring are preferred. The coil spring or flat spring is preferably made from a metal such as stainless steel or brass, and the rubber molding is preferably made from a synthetic resin such as fluororubber or silicon. Sealability can be adjusted by changing the diameter of a spring wire material.

The spacer is a means of reducing a volume other than a volume occupied by the sealing plug portion and the elastic body within the space of the dropping portion as much as possible. The spacer can exist in the space as a member independent of the sealing plug portion and the elastic body, or may be integrated with the sealing plug portion or the elastic body. In either case, the spacer must not prevent the sealing plug portion from being pressed against the opening in a fully liquid-filled state or the elastic body from acting on the sealing plug portion.

Figure 3:
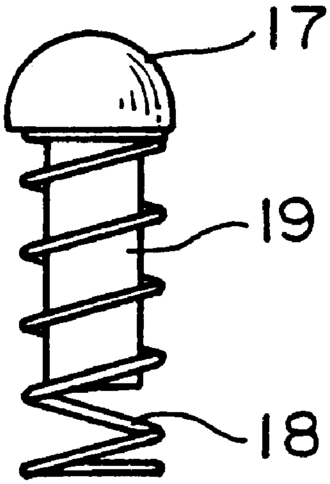
FIG. 3 is a schematic diagram of another embodiment of a pressure valve used in the present invention.

For example, when the sealing plug portion and the spacer are integrated with each other, as shown in FIG. 3, the spacer (19) is connected to the sealing plug portion (17) at a position where it does not prevent the sealing plug portion (17) from contacting the opening. In this case, the elastic body is indicated by (18).

The material of the spacer is selected from metals such as stainless steel and brass, synthetic rubber such as fluororubber and silicon rubber, polyolefins such as polyethylene and polypropylene, and synthetic resins such as fluororesin and urethane resin.

The spacer formed of a metal or a rubber molding is cylindrical, for example. The cylinder has cutouts or holes in the side surface so that the inside and outside of the side surface of the cylinder are communicated with each other through the cutouts and holes.

The spacer is preferably situated on the inner side of the elastic body within the space of the dropping portion.

The dropping portion (9) has the second thin tube (8). The dropping portion (9) encases the projecting portion (4) and the pressure valve, that is, the sealing plug portion (6) and the pressing member (7), and is fitted to, or joined to, the projecting portion (4). The opening (10) at one end of the second thin tube (8) is open to the inside of the dropping portion (9) and the opening (10') at the other end of the second thin tube (8) is open to the outside.

The dropping portion (9) can be made from a metal such as brass plated with nickel, and the second thin tube (8) can be a metal pipe such as a stainless steel pipe.

The second thin tube (8) of the dropping portion (9) penetrates the dropping portion (9) so that the interior space of the dropping portion (9) communicates with the outside air therethrough.

The second thin tube (8) and the dropping portion (9) can be produced as an integrated unit or separate units. In the latter case, the second thin tube (8) is inserted into a small hole formed in the center of the dropping portion (9) and fixed to the dropping portion (9) by caulking, for example.

The dropping container of the present invention has a movable plug (11) which can move in an axial direction in the cylindrical body (1). The material of the movable plug (11) is suitably selected from plastics and rubber which do not undergo change in qualities by the chemicals, that is, have chemical stability and dimensional stability and which can move along the inner wall of the cylindrical body in a fully liquid-filled state. Particularly when chemical resistance and solvent resistance are required, fluororubber and fluororesin are preferred. Although the fluororesin is a resin having relatively high lubricity, it has poor elasticity. Therefore, as shown in FIG. 1, it is advantageous to form one or more annular grooves (20) in the movable plug (11).

The annular groove may be fitted with a fluororubber-based O ring such as Kalrez or Viton as required.

The movable plug (11) is pressed and moved toward the direction of the closing portion (2) by the pressing means (12) provided in the second closing portion (13) fixed at the other end of the cylindrical body (1). The filling material filled in the cylindrical body is pressed forward by this movement, whereby the sealing plug portion of the pressure valve (6) pressing the opening (5) is slightly opened. As a result, the filling material moves into the space between the projecting portion (4) and the second thin tube (8) and is then dropped from the opening (10') at the end of the second thin tube (8).

The second closing portion (13) can be made from a metal, preferably brass plated with nickel. The second closing portion (13) is fixed at the other end of the cylindrical body (1) by a thermosetting resin-based adhesive. The pressing means (12) provided in the second closing portion (13) can be a screw or a piston, for example (screw in FIG. 1). In FIG. 1, the screw (12) turns and moves forward in a threaded portion formed in the center of the second closing portion (13), comes into contact with the movable plug (11) (does not contact in the FIG. 1) and presses the movable plug (11). The screw (12) can be driven by turning a knob (21) manually.

The dropping container of the present invention can have a cap (22) for covering a top end portion of the container. The cap (22) can be made from a synthetic resin such as Nylon 12. The cap (22) preferably has a rubber presser foot, for example, a fluororubber presser foot (23) at a position where it contacts the tip of the second thin tube (8) when it covers the top end portion of the dropping container. Or, the cap (22) can have an annular projection (24) which projects toward the inside of the cylindrical body (1) and the annular projection (24) allows to fix the cap (22) on the periphery of the dropping portion (9) detachably.

In the dropping container of the present invention, the pressure valve (6) is pressed against the opening (5) in the projecting portion (4) of the first thin tube (3) extending from the cylindrical body (1) to shut off the outside air completely from the filling material in the cylindrical body when not in use. Therefore, the deterioration of the filling material through its contact with the outside air can be prevented when it is preserved.

Since the pressure valve comprising the sealing plug portion, the elastic body and as required, the spacer, lies in the space of the dropping portion between the projecting portion (4) and the second thin tube (8), dead space can be made extremely small. Therefore, even if the filling material in the dead space deteriorates while it is preserved, in spite of the use of the cap, the amount of the deteriorated filling material is small and the further deterioration of the filling material can be prevented completely.

The dropping container of the present invention can be exemplified by a syringe comprising a cylindrical body formed of a hard glass tube having an inner diameter of 5 mm, an outer diameter of 8 mm and a length of 70 mm; the first thin tube made from brass and having an inner diameter of 1 mm; the second thin tube of the dropping portion made from iron plated with nickel and having an inner diameter of 0.3 mm and a connection portion having a length from the end of the second thin tube to the cylindrical body of about 20 mm (a portion of the thin tube projecting forward from the dropping portion being about 6 mm); a screw having a diameter of 3 mm; a knob having a diameter of 10 mm; the spring of a spacer 7 made from an elastic wire material having a diameter of 0.4 mm; and a cap having an outer diameter of 8 mm and a length of about 22 mm. The size of the dropping container is not limited to the size of this example. However, it has been found that the dropping container of this size in the above example is extremely easy to use when actually in use.

EXAMPLE 1

A partial oxide of tributylboron containing about 30 wt % of acetone was dropped from the above dropping container comprising a Teflon R ball (fluororesin having a diameter of ⅛ inch) as the sealing member (14). Dropping could be carried out smoothly. There was no liquid leakage after use.

EXAMPLE 2

Dropping was carried out in the same manner as in Example 1 except that a 18-8 stainless steel ball (diameter of ⅛ inch) was used in place of the Teflon R ball. Dropping could be carried out smoothly. Leakage of a trace amount of a solution occurred after use but stopped immediately.

The dropping container of the present invention perfectly prevents entry of air from the outside, has small dead space and can drop a required amount of a chemical easily. Therefore, the dropping container of the present invention does not deteriorate a liquid chemical substance which is filled in the container and deteriorates upon its contact with the outside air even when it is preserved for a long time.

What is claimed is:

1. A dropping container comprising:

(a) a cylindrical body (1);

(b) a first closing portion (2) having a first end extending within said cylindrical body for closing one end of the cylindrical body (1), the first closing portion (2) having a projection portion (4) which projects from the cylindrical body (1) in an axial direction of the cylindrical body (1), the first closing portion (2) and the projecting portion (4) having an unobstructed first thin tube (3) extending therethrough, the first thin tube (3) having an opening (5) at one end thereof leading into a space adjacent the projecting portion (4) and an opening (5') at the other end thereof leading into the cylindrical body (1);

(c) a pressure valve disposed in the space and comprising a sealing plug portion (6), formed of an elastic body or a rigid body, for closing the opening (5) of the projection portion (4) such that it can be opened by pressure and a pressing member (7), formed of an elastic body, for pressing the sealing plug portion (6) against the opening (5);

(d) a dropping portion (9) having said space therein and a second thin tube (8) therein, the dropping portion (9) encasing the projecting portion (4) and the pressure valve and is fitted to the projection portion (4), an opening (10) of the second thin tube (8) at one end being open to the space within the dropping portion (9) and an opening (10') thereof at the other end being open to the outside, wherein said unobstructed first thin tube, said pressure valve disposed in said space and said second tube are situated in this order in the direction from the cylindrical body to the dropping portion;

(e) a plug (11) movable in the axial direction, that is situated within the cylindrical body (1); and (f) a second closing portion (13) which is fixed to the other end of the cylindrical body (1) and has pressing means (12) for pressing the movable plug (11) towards the first closing portion (2).

2. The dropping container of claim 1, wherein the opening and the sealing plug portion of the pressure valve are in surface contact or circular line contact with each other to close the opening.

3. The dropping container of claim 1, wherein the spacer reduces the dead space in the space for accommodating the pressure valve.

4. The dropping container of claim 1, wherein the pressing member is selected from the group consisting of a coil spring, a flat spring and an elastic body of natural or synthetic rubber.

5. The dropping container of claim 1, wherein the sealing plug portion of the pressure valve is formed of an elastic body made from natural or synthetic rubber, or a rigid body made from fluororesin, stainless steel, polyolefin resin or metal oxide.

6. The dropping container of claim 1, which has a cap (22) for covering a top end portion of the container, said cap having a rubber pressure foot at a position where the cap contacts the tip of the second thin tube (8).

7. The dropping container of claim 1, which is a syringe.

* * * * *